(12) United States Patent
Berk et al.

(10) Patent No.: US 11,707,454 B2
(45) Date of Patent: Jul. 25, 2023

(54) TOPICAL ROFLUMILAST FORMULATION HAVING ANTIFUNGAL PROPERTIES

(71) Applicant: ARCUTIS BIOTHERAPEUTICS, INC., Westlake Village, CA (US)

(72) Inventors: David Reuben Berk, Westlake Village, CA (US); Patrick Eugene Burnett, Westlake Village, CA (US); Saori Kato, Westlage Village, CA (US); David W. Osborne, Fort Collins, CO (US)

(73) Assignee: Arcutis Biotherapeutics, Inc., Westlake Village, CA (US)

( * ) Notice: Subject to any disclaimer, the term of this patent is extended or adjusted under 35 U.S.C. 154(b) by 0 days.

(21) Appl. No.: 17/542,072

(22) Filed: Dec. 3, 2021

(65) Prior Publication Data

US 2022/0175743 A1 Jun. 9, 2022

Related U.S. Application Data

(60) Provisional application No. 63/121,299, filed on Dec. 4, 2020.

(51) Int. Cl.
| | | |
|---|---|---|
| *A61K 31/44* | (2006.01) | |
| *A61K 9/00* | (2006.01) | |
| *A61K 31/137* | (2006.01) | |
| *A61K 31/27* | (2006.01) | |
| *A61K 31/343* | (2006.01) | |
| *A61K 31/4174* | (2006.01) | |
| *A61K 31/4418* | (2006.01) | |
| *A61K 31/496* | (2006.01) | |
| *A61K 31/506* | (2006.01) | |
| *A61K 31/60* | (2006.01) | |
| *A61K 33/04* | (2006.01) | |
| *A61K 45/06* | (2006.01) | |
| *A61K 47/06* | (2006.01) | |
| *A61K 47/10* | (2017.01) | |
| *A61K 47/14* | (2017.01) | |
| *A61K 47/24* | (2006.01) | |

(52) U.S. Cl.
CPC ............ *A61K 31/44* (2013.01); *A61K 9/0014* (2013.01); *A61K 31/137* (2013.01); *A61K 31/27* (2013.01); *A61K 31/343* (2013.01); *A61K 31/4174* (2013.01); *A61K 31/4418* (2013.01); *A61K 31/496* (2013.01); *A61K 31/506* (2013.01); *A61K 31/60* (2013.01); *A61K 33/04* (2013.01); *A61K 45/06* (2013.01); *A61K 47/06* (2013.01); *A61K 47/10* (2013.01); *A61K 47/14* (2013.01); *A61K 47/24* (2013.01)

(58) Field of Classification Search
CPC ...... A61K 31/44; A61K 31/137; A61K 31/27; A61K 31/343; A61K 31/4174
See application file for complete search history.

(56) References Cited

FOREIGN PATENT DOCUMENTS

WO 2014/130922 A1 8/2014

OTHER PUBLICATIONS

Marcon et al., "In Vitro Activity of Systemic Antifungal Agent against Malassezia furfur", Antimicrobial Agents and Chemotherapy, vol. 31, No. 6, pp. 951-953 (1987).*
Petranyi et al., "Antifungal Activity of the Allylamine Derivative Terbinafine In Vitro", Antimicrobial Agents and Chemotherapy, vol. 31, No. 9, pp. 1365-1368 (1987).*
Sugita et al., "Antifungal Activities of Tacrolimus and Azole Agents against the Eleven Currently Accepted *Malassezia* Species", Journal of Clinical Microbiology, vol. 43, No. 6, pp. 2824-2829.*
Notification of Transmittal of the International Search Report and the Written Opinion of the International Searching Authority, issued in PCT/US2021/061871, dated Apr. 5, 2022, 12 pages.

* cited by examiner

*Primary Examiner* — Kevin E Weddington
(74) *Attorney, Agent, or Firm* — Rothwell, Figg, Ernst & Manbeck, P.C.

(57) ABSTRACT

The present invention is directed to a method of treating a fungal infection comprising administering topically, to a subject in need thereof, an anti-fungal effective amount of roflumilast. Preferably, topically administered roflumilast is used to treat fungal infections, fungal growth of and/or hypersensitivity to the fungi *Malassezia* spp. Patients may also be suffering from seborrheic dermatitis, dandruff, dupilumab facial redness, *Tinea versicolor, Pityriasis versicolor, Tinea circinata, Tinea pedis, Tinea unguium, Tinea manus, Tinea cruris, Tinea corporis, Tinea faciei, Tinea capitis*, and/or *Tinea incognito*. Topically administered roflumilast is a quick and effective antifungal agent and presents a viable alternative to current antifungal treatments.

17 Claims, 1 Drawing Sheet

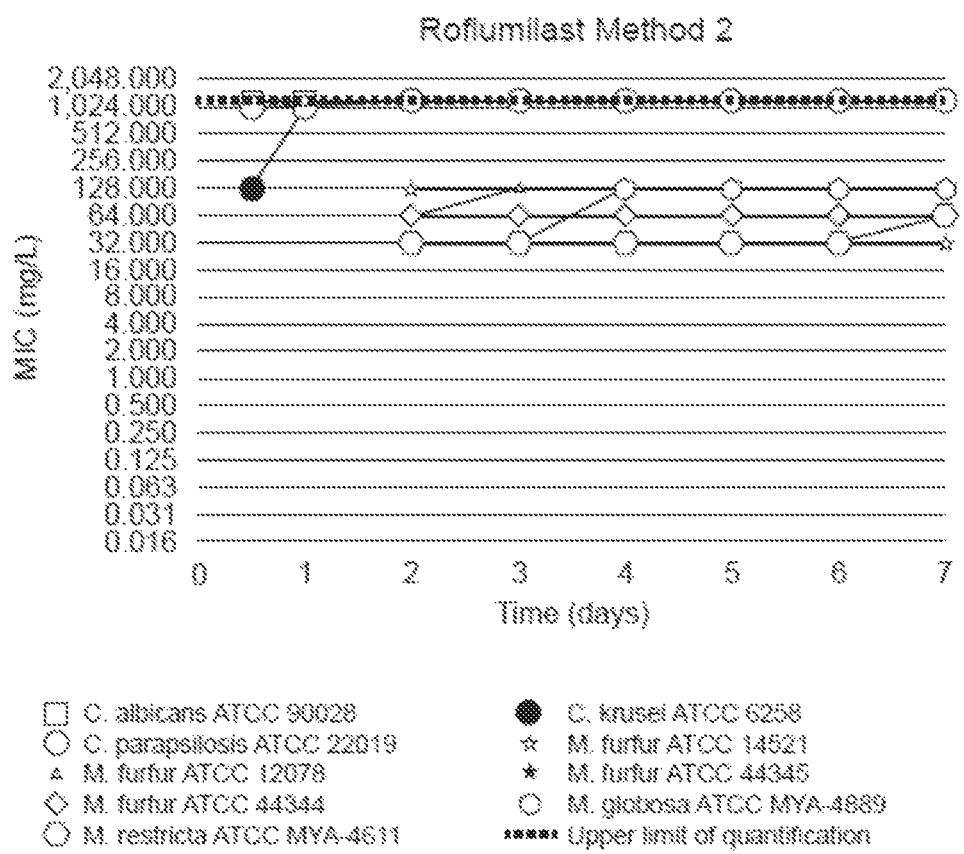

TOPICAL ROFLUMILAST FORMULATION HAVING ANTIFUNGAL PROPERTIES

CROSS REFERENCE TO RELATED APPLICATION

This application claims the benefit of Patent Application No. 63/121,299 filed on Dec. 4, 2020, the disclosure of which is incorporated herein in its entirety by reference.

FIELD OF THE INVENTION

The invention pertains to the use of a PDE4 inhibitor having antifungal properties to treat fungal infections, inflammation caused by fungal infections or the treatment of fungal infections and fungal overgrowth of hair, skin or nails. More particularly, the invention pertains to a method of treating fungal infections using topically administered roflumilast.

BACKGROUND OF INVENTION

Fungal Infections of Skin, Nails, and Hair

Bacteria, viruses, and fungi are all part of the microflora of healthy human and animal skin. *Malassezia* spp. is a genus of microscopic, single-celled fungi (or yeasts) that is one of the most common fungi naturally found on the skin surface. The most common and well-known species in the genus *Malassezia* are *Malassezia furfur* ("*M. furfur*") *Malassezia globosa, Malassezia restricta* and *Malassezia pachydermatis*.

The *Malassezia* species generally lives on the superficial layers of the dermis, predominately on sebum-rich areas such as the trunk, face, scalp, ears, forehead, nasolabial folds, *glabella*, and beard area. It is a commensal organism of the skin microbiota, generally known for strengthening the body's defenses and helping to protect the immune system from dangerous pathogens. Specifically, it has been demonstrated that *Malassezia* species stimulates the immune system to produce the cytokine interleukin-17, among other cytokines, to mediate induction of proinflammatory molecules which participate in the control of these pathogens and prevent fungal overgrowth on the skin. However, if this immunologic process is disrupted, for instance, if the cytokine is not released or if the immune cells that produce interleukin-17 are missing, *Malassezia* species will grow and infest the skin. The fungus effectively becomes an allergen on the skin, creating an imbalance of the skin microflora, and ultimately triggers an overreaction of the immune system with respect to inflammation. *Malassezia* species may also proliferate uncontrollably and gain pathogenic capabilities when changing from a yeast to a hyphal form (a branched, filamentous fungi structure) during its lifetime, through unknown molecular changes.

While the causative relationship between fungal commensalism and disease manifestation remains incomplete, pathogenic *Malassezia* species have been associated with a variety of dermatological conditions, including seborrheic dermatitis, dandruff, pityrosporum folliculitis, atopic dermatitis, *Tinea versicolor* and *Pityriasis versicolor* generally presenting clinically as skin lesions in the form of hypo- or hyperpigmented macules, patches, or scaly papules or plaques, with variable erythema. For seborrheic dermatitis, in addition to abnormal immune response or fungal activity, it is believed that *Malassezia* species may be implicated in the disease pathogenesis as a result of excessive sebum production, which may trigger the lipophilic yeast into overgrowth. Other potential pathologic mechanisms and potential disease factors that may trigger the response to *Malassezia* species include defective skin barrier function, hormonal fluctuations (especially those that affect sebum production), neurologic factors, and exogenous factors such as lack of sunlight and eating disorders.

Pathogenic *Malassezia* species have also been linked to dupilumab facial redness (DFR) and inflammation. Dupilumab inhibits IL-4 and IL-13 by blocking the IL-4 receptor a and is the first biological treatment for moderate to severe atopic dermatitis. One of the known adverse effects of dupilumab treatment is the development of an eczematous facial rash months after the initiation of dupilumab treatment. DFR has been found to affect approximately 5-10% of patients treated with dupilumab in practice and is exacerbated by continued administration of dupilumab. Patients are often reluctant to stop dupilumab treatment due to the significant improvement in their atopic dermatitis. In de Beer, et. al. JAAD CASE REPORTS Vol 5 (10) pages 888-891 (2019), *Malassezia* hypersensitivity was suggested as a possible cause for DFR because *M. furfur* can easily penetrate the disturbed skin barrier function (as a result of the atopic dermatitis) and locally impair and activate keratinocytes, thereby enhancing inflammation (also see Strong, Colby, Oral and Topical Antifungals Beneficial for Dupilumab Facial Redness in Atopic Dermatitis, Dermatology Advisor, Published online Oct. 27, 2021; dermatologyadvisor.com/home/topics/dermatitis/oral-and-topical-antifungals-beneficial-for-dupilumab-facial-redness-in-ad/). Dupilumab facial redness has been treated with corticosteroids and topical calcineurin inhibitors. In a recent Dermatology Therapy article, oral and topical antifungals were found to be effective for patients with atopic dermatitis (AD) who develop dupilumab facial redness (DFR) and inflammation after receiving dupilumab treatment (Ordóñez-Rubiano M F, Casas M, Balaguera-Orjuela V, et al. Dupilumab facial redness: Clinical characteristics and proposed treatment in a cohort. Dermatol Ther. Published online Sep. 21, 2021. doi:10.1111/dth.15140). These results provide a stronger link between pathogenic *Malassezia* species and DFR.

While fungi such as *Malassezia* species cause infections limited to the outermost layers of the skin and hair (superficial mycoses), other fungi cause cutaneous mycoses by penetrating to the keratinized layers of the skin, hair and nails and triggering pathologic changes in the host. For instance, fungi called dermatophytes can parasitize the horny cell layer, causing dermatophytosis.

Dermatophytes are divided into three genera: *Trichophyton, Microsporum*, and *Epidermophyton*. The genus *Trichophyton* comprises species *T. rubrum, T. mentagrophytes, T. verrucosum, T. violaceum, T. schoenleinii, T. tonsurans, T. concentricum*, and *T. equinum*. The genus *Microsporum* comprises species *M. canis, M. gypseum, M. audouinii, M. cookei, M. equinum, M. ferrugineum, M. gallinae*, and *M. nanum*. The genus *Epidermophyton* comprises species *E. floccosum*. The most common dermatophytes are *T. rubrum, T. tonsurans* and *T. mentagrophytes*. Because dermatophytes feed on keratin, they usually infect the epidermal horny cell layer, nails and hair follicles, causing superficial lesions. The name of the dermatophytosis (fungal skin disease) differs by the location. Disease names with their associated common name in parentheses are: *Tinea pedis* (athlete's foot), *Tinea unguium* or onychomycosis, *Tinea manus, Tinea cruris* (jock itch), *Tinea corporis* (serpigo), *Tinea faciei, Tinea capitis* (scald head) and *Tinea incognito*.

A specific example of a fungal infection caused by the fungi and yeasts discussed above is onychomycosis (primarily by the dermatophytes including *Trichophyton* spp., *Epidermophyton* spp., and *Microsporum* spp.). Onychomycosis is a chronic, persistent fungal, yeast, and/or mold infection of the nail bed and plate which causes thickening and discoloration of the nail, sometimes accompanied by pain and disability. Fungal infections affecting the nails or scalp are very difficult to treat due to fungal infection in follicle roots or under the nail itself. Onychomycosis is also particularly difficult to treat, due to the length of time it takes the nail to grow and the impenetrability of the nail plate. A similar situation occurs with *Tinea capitis* where the scalp and hair shafts are infected. Thus, in onychomycosis and *Tinea capitis*, eradication of symptoms is very slow and may take several months or up to a year or longer.

Conventional Treatments for Fungal Infections

Fungal infections are currently managed using topical antifungal agents, keratolytics (peeling agents that may reduce flaking and scaling), and/or oral drugs. However, these treatments frequently fail or pose safety concerns that limit their use. For instance, although orally administered drugs are generally more effective than topically applied drugs, because they act systemically rather than locally, the side effects of orally administered drugs can be much more severe. The known side effects are very serious, and include hepatic and/or cardiac toxicity, headaches, dizziness, extreme tiredness, lack of energy, flu-like symptoms, difficulty breathing or swallowing, seizures, heartburn, depression, upset stomach, and adverse drug interactions, just to name few. Similarly, while topical corticosteroids are effective anti-inflammatory agents, the long term use of mid-to-high-potency corticosteroids has been known to cause burning, stinging, swelling, redness, discoloration, and skin sensitivity, and may trigger or worsen other skin disorders such as acne, rosacea, perioral dermatitis, telangiectasia (small broken blood vessels), and striae (stretch marks).

Common topical antifungal treatments include drugs containing ciclopirox, drugs containing miconazole (Daktarin®, Micatin® & Monistat®), clotrimazole (Canesten®, Hydrozole®), butenafine (Lotrimin Ultra®, Mentax®), terbinafine (Lamisil®), amorolfine (Curanail®, Loceryl®, Locetar®, and Odenil®), naftifine (Naftin®), tolnaftate (Tinactin®), efinaconazole (Jublia®) and ketoconazole (Nizoral®). Others that may also be used to clear up fungal infections are ethylparaben, flucytosine, salicylic acid, selenium sulfide, and undecylenic acid.

Ciclopirox olamine (also called Batrafen® Loprox®, Penlac® and Stieprox®) is a synthetic antifungal agent for topical dermatologic use that has a high affinity for trivalent metal cations. Ciclopirox typically comes as a solution to apply to the scalp, nails and the skin immediately surrounding and under the nails. However, while Ciclopirox may improve the condition of nails, it may not completely cure nail fungus. Moreover, it may take 6 months or longer before there is any indication that the infected nails are improving. Furthermore, ciclopirox topical solution is flammable, and may include side effects such as redness at the application site, irritation, itching, burning, blistering, swelling, or oozing at the application site, pain at the affected nail(s) or surrounding area, discoloration or change in shape of nail(s), and ingrown nail(s).

Ketoconazole cream (Nizoral®) is generally used to treat *Tinea corporis* (ringworm; fungal skin infection that causes a red scaly rash on different parts of the body), *Tinea cruris*, *Tinea pedis*, *Tinea versicolor* (fungal infection that causes brown or light colored spots on the chest, back, arms, legs, or neck), and yeast infections of the skin. Prescription ketoconazole shampoo is used to treat *Tinea versicolor*. However, ketoconazole may cause side effects, such as changes in hair texture, blisters on scalp, dry skin, itching, oily or dry hair or scalp, irritation, itching, or stinging at the application site, rash, hives, difficulty breathing or swallowing, and redness, tenderness, swelling, pain, or warmth at the application site.

Thus, there is a need in the art for improved treatment options for patients affected by fungal infections, including fungal infections of the nails, hair, and the skin. Specifically, there is a significant need for highly effective fungicidal agents that a) quickly and completely eradicate fungal infections of the nails, hair, and the skin, and b) reduce facial redness or inflammation due to a *Malassezia* infection, treatment of a *Malassezia* infection and/or *Malassezia* hypersensitivity caused by the treatment of moderate to severe atopic dermatitis. The present invention provides topically administered roflumilast as a viable and successful alternative to current antifungal treatments.

Topically Administered Roflumilast

Roflumilast is known to be suitable for the treatment of inflammatory disorders. Compositions containing roflumilast are used in human and veterinary medicine and have been proposed for the treatment and prophylaxis of diseases including but not limited to: inflammatory and allergen-induced airway disorders (e.g. bronchitis, asthma, COPD); dermatoses (e.g. proliferative, inflammatory and allergen induced skin disorders), and generalized inflammations in the gastrointestinal region (e.g. Crohn's disease and ulcerative colitis).

Roflumilast and its synthesis were described in U.S. Pat. No. 5,712,298 (the "'298 patent"), incorporated herein by reference.* It has long been recognized that pharmaceutical compounds having phosphodiesterase (PDE)-inhibiting properties, such as roflumilast, are useful for treating psoriasis and atopic dermatitis ('298 patent, col 11 lines 52-61) and other chronic inflammatory and allergen-induced dermatoses. For treatment of such dermatoses, roflumilast emulsions, suspensions, gels or solutions for topical application have been described ('298 patent, col 12, lines 37-64).

* Unless otherwise indicated, references incorporated herein by reference are incorporated in their entireties for all purposes.

Topical application of potent pharmacological agents like roflumilast for treating skin diseases has been found to provide superior delivery, lower systemic exposure and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin.

SUMMARY OF THE INVENTION

In accordance with the present invention, it has been discovered that topically administered roflumilast exhibits anti-fungal properties, in addition to its known anti-inflammatory properties as a PDE4 inhibitor. These characteristics make topical roflumilast an optimal treatment method for treating fungal infections, fungal overgrowth of hair, skin or nails and inflammation due to fungal hypersensitivity. Topical roflumilast has exhibited significant and fast reduction of the *Malassezia* fungus and a high seborrheic dermatitis treatment success rate, with an Investigator Global Assessment Success rate at week 8 for 0.3% roflumilast of 73.8% compared to a vehicle foam rate of 40.9%. The quick and successful treatment results indicate that topically administered roflumilast is an effective antifungal agent and presents a viable alternative to current antifungal treatments.

BRIEF DESCRIPTION OF THE DRAWINGS

FIG. 1 shows the results of an in vitro micro-dilution susceptibility assay for testing the anti-fungal activity of roflumilast. As shown in FIG. 1 and Table B roflumilast has been shown to have antifungal activity against *Malassezia* species.

DETAILED DESCRIPTION OF THE INVENTION

Roflumilast is a compound of the formula (I)

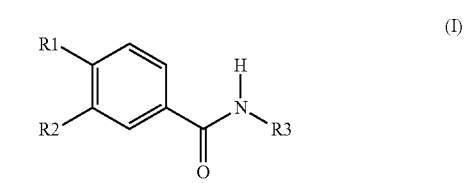

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamid-e (INN: roflumilast).

Hexylene glycol (PharmaGrade. USP/NF) is 2-methyl-2,4-pentanediol of the formula (II).

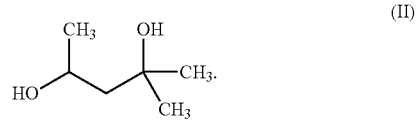

The emulsifier blend of cetearyl alcohol (CAS 67762 30 0), dicetyl phosphate (CAS 2197 63 9) and ceteth-10 phosphate (CAS 50643-20-4) is manufactured by Croda under the tradename CRODAFOS™ CES. CRODAFOS™ CES PHARMA is manufactured using the same starting materials and process, but undergoes enhanced quality control and release testing and uses the nomenclature cetearyl alcohol, cetearyl phosphate and ceteareth-10 phosphate in keeping with standard practice for naming pharmaceutical excipients. This commercially available emulsifier blend is a self-emulsifying wax that is predominately the waxy material cetearyl alcohol (which is a mixture of cetyl alcohol ($C_{16}H_{34}O$) and stearyl alcohol ($C_{18}H_{38}O$)) combined with 10-20% dicetyl phosphate (cetearyl phosphate) and 10-20% ceteth-10 phosphate (ceteareth-10 phosphate). Self-emulsifying waxes form an emulsion when blended with water. When CRODAFOS™ CES is added to water it spontaneously forms an emulsion having a pH of about 3. Sodium hydroxide solution is added to increase the pH to the desired value.

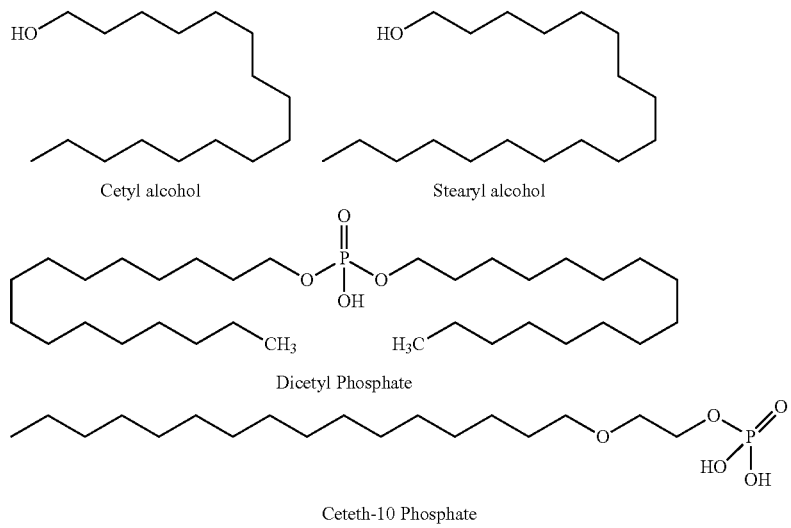

The topical roflumilast product formulations that may be used to treat fungal infections or fungal overgrowth include but are not limited to aerosols, foams, sprays, emulsions (which can also be called creams, lotions, or ointments), gels (two phase or single phase), liquids, ointments, pastes, shampoos, suspensions, and systems. These are the tier two terms within compendia taxonomy for dosage forms containing pharmaceutical active ingredients (US Pharmacopeia <1151>). In a preferred embodiment, the topical roflumilast product formulation comprises a foam. More preferably, the topical roflumilast product formulation comprises ARQ 154 Foam.

Roflumilast can be prepared by methods known in the art (e.g. see the '298 patent and U.S. application Ser. No. 14/075,035). Roflumilast formulations are also disclosed in U.S. Pat. No. 9,884,050, U.S. application Ser. No. 15/712,900, U.S. application Ser. No. 16/426,492, U.S. application Ser. No. 16/426,492, U.S. application Ser. No. 16/563,435 and U.S. application Ser. No. 16/778,845, the disclosures of which are herein incorporated in their entirety.

Preferably, the topical formulations for treating fungal infections comprise compositions containing 0.005-2.0% roflumilast, preferably 0.3%, that may be in one of the following forms:

An oil-in-water emulsion: The product may be a formulation in which hexylene glycol, a self-emulsifying wax blend of dicetyl phosphate and ceteth-10 phosphate, and/or a solvent is added to an emulsion comprising a discrete phase of a hydrophobic component and a continuous aqueous phase that includes water and optionally one or more polar hydrophilic excipients as well as additional solvents, co-solvents, salts, surfactants, emulsifiers, and other components. These emulsions may include water-soluble or water-swellable polymers that help to stabilize the emulsion. Preferably, the emulsifier is a self-emulsifying wax blend of dicetyl phosphate and ceteth-10 phosphate.

An aerosol foam: The product may be produced when an oil-in-water emulsion product concentrate is mixed with a liquid propellant and the propellant blends with the internal oil phase of the emulsion. The emulsifier in the oil-in-water emulsion also serves as a foaming agent. A quick breaking foam creates a foam when emitted from the container but the foam collapses in a relatively short time. This type of foam is used to apply the product concentrate to a large area without having to manually rub or spread the product. Also, the active drug is more rapidly available because the foam quickly collapses. Stable foams are produced when emulsifiers are used that have limited solubility in both the organic and aqueous phases. Emulsifiers or emulsifying waxes concentrate at the interface between the propellant/oil phase and the aqueous phase to form a thin film referred to as the "lamella." It is the specific composition of this lamella that dictates the structural strength and general characteristics of the foam. Thick and tightly layered lamellae produce very structured foams which are capable of supporting their own weight. One or more polar hydrophilic excipients as well as additional solvents, co-solvents, salts, surfactants, emulsifiers, and other components may be added to the emulsion product concentrate. These emulsions may include water-soluble or water-swellable polymers that help to stabilize the emulsion. Preferably, the emulsifier is a self-emulsifying wax blend of dicetyl phosphate and ceteth-10 phosphate.

Thickened Aqueous gels: These systems include an aqueous phase which has been thickened by suitable natural, modified natural, or synthetic thickeners such as described below. Alternatively, the thickened aqueous gels can be thickened using suitable polyethoxylate alky chain surfactants or other nonionic, cationic, or anionic systems.

Thickened Hydroalcoholic gels: These systems include a blend of water and alcohol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

Hydrophilic gels: These are systems in which the continuous phase includes at least one water soluble or water dispersible hydrophilic component other than water. The formulations may optionally also contain water up to 60% by weight. Higher levels may be suitable in some compositions. Suitable hydrophilic components include one or more glycols such as polyols such as glycerin, propylene glycol, butylene glycols, polyethylene glycols (PEG), random or block copolymers of ethylene oxide, propylene oxide, and/or butylene oxide, polyalkoxylated surfactants having one or more hydrophobic moieties per molecule, silicone copolyols, blend of ceteareth-6 and stearyl alcohol as well as combinations thereof, and the like.

A water-in-oil emulsion: The compositions may be formulations in which roflumilast is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion. Preferably, the emulsifier is a self-emulsifying wax blend of dicetyl phosphate and ceteth-10 phosphate.

A hydrophilic or hydrophobic ointment: The compositions are formulated with a hydrophobic base (e.g. petrolatum, thickened or gelled water insoluble oils, and the like) and optionally having a minor amount of a water soluble phase. Hydrophilic ointments generally contain one or more surfactants or wetting agents.

Solvents

Compositions according to the present invention may include one or more solvents or co-solvents to obtain the desired level of active ingredient solubility in the topical product. The solvent may also modify skin permeation or the activity of other excipients contained in the formulation. Solvents include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, polyethylene glycol, glycerol, propylene glycol and SD alcohol. When treating a patient with an inflammatory condition, the solvent is preferably not ethanol, isopropyl alcohol or denatured alcohol.

Moisturizers

Compositions according to the present invention may include a moisturizer to increase the level of hydration. The moisturizer can be a hydrophilic material including humectants or it can be a hydrophobic material including emollients. Suitable moisturizers include but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, white petrolatum, isopropyl palmitate, and stearyl alcohol.

Surfactants and Emulsifiers

Compositions according to the present invention optionally can include one or more surfactants to emulsify the composition and to help wet the surface of the actives or excipients. As used herein the term "surfactant" means an amphiphile (a molecule possessing both polar and nonpolar regions which are covalently bound) capable of reducing the surface tension of water and/or the interfacial tension between water and an immisicible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-2, ceteth-20, ceteth-23, choleth-24, cocamide ether sulfate, cocamine oxide, coco betaine, coco diethanolamide, coco monoethanolamide, coco-caprylate/caprate, disodium cocoamphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax. Preferably, the emulsifier is a self-emulsifying wax blend of dicetyl phosphate and ceteth-10 phosphate.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, carboxy vinyl copolymer, carboxymethylcellulose, carboxypolymethylene, carrageenan, guar gum, hydroxyethyl cellulose, hydroxypropyl cellulose, microcrystalline wax, and methylcellulose, Additional Components Compositions according to the present invention may be formulated with additional components such as fillers, carriers and excipients conventionally found in cosmetic and pharmaceutical topical products. In a preferred embodiment, the fillers, carriers and excipients are suitable for topical administration. Additional components including but not limited to antifoaming agents, preservatives (e.g. p-hydroxybenzoic esters, benzyl alcohol, phenylmercury salts, chlorocresol, methylparaben, propylparaben), antioxidants, sequestering agents, stabilizers, buffers, pH adjusting solutions, skin penetration enhancers, film formers, dyes, pigments, diluents, bulking agents, fragrances and other excipients to improve the stability or aesthetics, may be added to the composition.

Compositions according to the present invention may be formulated with additional active agents depending on other conditions being treated. The additional active agents include but are not limited to NSAIDs (e.g. Aspirin, Ibuprofen, Ketoprofen, Naproxen), Apremilast, JAK inhibitors (e.g. Tofacitinib, Ruxolitinib, Oclacit), leukotriene inhibitors (e.g. Zileuton, Zafirlukast, Montelukast), mast cell stabilizers (e.g. Nedocromil, Cromolyn sodium, Ketotifen, Pemirolast), Anthralin (dithranol), Azathioprine, Tacrolimus, Pimecrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Tapinarof, Colchicine, bronchodilators (e.g. beta-agonists, anticholinergics, theophylline), and antibiotics (e.g. erythromycin, ciprofloxacin, metronidazole).

Compositions according to the present invention may be formulated with additional antifungal agents according to the specific fungal infection being treated. The additional antifungal agents include but are not limited to: drugs containing miconazole (Daktarin, Micatin & Monistat), ciclopirox olamine (Batrafen, Loprox, Penlac, and Stieprox), clotrimazole (Canesten, Hydrozole), butenafine (Lotrimin Ultra, Mentax), terbinafine (Lamisil, Terbisil, Zabel), amorolfine (Curanail, Loceryl, Locetar, and Odenil), naftifine (Naftin), tolnaftate (Tinactin), ketoconazole (Nizoral), griseofulvin, imidazoles (bifonazole, clomidazole, econazole, fenticonazole, isoconazole, miconazole, oxiconazole, sertaconazole, sulconazole, tioconazole), triazole (fluconazole, itraconazole, posaconazole (Noxafil), voriconazole (Vfend)), benzimidazole (thiabendazole), ethylparaben, flucytosine, salicylic acid, selenium sulfide, and undecylenic acid. Alternatively, the additional anti-fungal agent can be administered as a separate composition.

Compositions according to the present invention may be formulated with common topical anti-inflammatory agents including, but not limited to, Diflucortolone valerate, Fluocinonide, Flurandrenolide, Halobetasol propionate, Amcinonide, Desoximetasone, Diflorasone, Halcinonide, Betamethasone valerate, Diflorasone diacetate, Fluticasone propionate, Mometasone furoate, Triamcinolone acetonide, Clocortolone pivalate, Fluocinolone acetonide, Fluticasone propionate, Hydrocortisone valerate, Mometasone furoate, Desonide, Hydrocortisone butyrate, Hydrocortisone probutate, Hydrocortisone valerate, Prednicarbate, Betamethasone dipropionate augmented Clobetasol propionate, Alclometasone dipropionate, Hydrocortisone (base, ≤2%), Hydrocortisone (base, <2%), calcineurin inhibitors and Hydrocortisone acetate. Alternatively, the anti-inflammatory agent can be administered as a separate composition.

Administration and Dosage

The compositions according to the present invention can be administered by any suitable administration route including but not limited to oral, rectal, parenteral (e.g. intradermal, subcutaneous, intramuscular, intravenous, intramedullary, intra arterial, intrathecal, epidural), ocular, inhalation, nebulization, cutaneously (topically), transdermally, and mucosally (e.g. sublingual, buccal, nasally). In a preferred embodiment, the composition is administered topically.

Suitable pharmaceutical dosage forms include but are not limited to emulsions, suspensions, sprays, oils, ointments, fatty ointments, creams, pastes, gels, foams transdermal patches and solutions (e.g. injectable, oral).

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit.

The composition preferably contains hexylene glycol in an amount of between 0.1% and 20% w/w, more preferably between 0.25% and 8% w/w and most preferably between 0.5% and 2% w/w.

The composition preferably contains a phosphate ester surfactant in the formulation which is in an amount sufficient to produce a stable emulsion having uniform globule size. The concentration of the phosphate ester surfactant generally may be any concentration between 1.0% to 25% w/w. The preferred concentration can be different for different administration forms. In a preferred embodiment, when the formulation is a cream or ointment, the concentration of the phosphate ester surfactant is between 2.5% and 20%, with a more preferred concentration range between 5% and 15%, and a most preferred concentration being about 10% w/w. When the formulation is in the form of a foam, the concentration is preferably between 1.0%-10%, more preferably between 1.0%-10%, and most preferably 2%. Preferably the phosphate ester surfactant is provided in a self-emulsifying wax blend of dicetyl phosphate and ceteth-10 phosphate.

The composition preferably contains a solvent in an amount sufficient to obtain the desired level of active ingredient solubility in the formulation. The solvent is preferably is in an amount of 10-30% (w/w). The ratio of solvent to water is preferably from 1:10 to 20:1. Preferably, the solvent is diethylene glycol monoethyl ether (DEGEE).

The topical formulation containing roflumilast, is applied to the skin in an amount that is sufficient to obtain the desired pharmacologic effect, which typically is to ameliorate the signs and/or symptoms of a fungal infection. The amount of the formulation that is applied may vary depending on the amount of roflumilast that is contained within the formulation, the concentration of the roflumilast within the formulation, and the frequency in which the formulation is intended to be applied. Generally, the formulation is applied with a frequency between weekly to several times daily, preferably between every other day to three times daily, and most preferably one or two times daily.

The composition can be used in veterinary and in human medicine for the treatment and prevention of fungal infections of the skin, nails, and hair. Preferably the composition is used to treat fungal infections or fungal overgrowth of the fungi *Malassezia* spp., *Trichophyton* spp., *Epidermophyton* spp., or *Microsporum* spp. The *Malassezia* spp. is preferably *Malassezia furfur* ("*M. furfur*") *Malassezia globosa, Malassezia restricta* and/or *Malassezia pachydermatis* More preferably, the composition is used to treat proliferative and inflammatory fungal infections such as seborrheic dermatitis, dandruff, dupilumab facial redness, *Tinea versicolor, pityriasis versicolor, Tinea circinata*, and dermatophytosis including *Tinea pedis* (athlete's foot), *Tinea unguium* or onychomycosis, *Tinea manus, Tinea cruris* (jock itch), *Tinea corporis* (serpigo), *Tinea faciei, Tinea capitis* (scald head) and *Tinea incognito*.

The formulation for topical application containing roflumilast, may be prepared by processes typically used in the field of manufacture of pharmaceutical formulations for topical application. In order to make a single-phase formulation, such as a liquid, the constituents of the formulation may be combined and mixed until a homogenous solution or suspension of the active ingredient is obtained. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The one or more drug actives may be dissolved (molecularly dispersed), complexed, or associated with an excipient or other active, or may be particulate (amorphous or crystalline). The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

The following examples are provided to enable those of ordinary skill in the art to make and use the methods and compositions of the invention. These examples are not intended to limit the scope of what the inventors regard as their invention. Additional advantages and modifications will be readily apparent to those skilled in the art.

Example 1

A formulation of the invention was made using a sample of ARQ 154 Foam, comprising roflumilast at a concentration of 0.3% w/w and a vehicle (0.2% MP, 0.05% PP), hereinafter referred to as Formulation 1. Formulation 1 was topically administered to $6.5 \times 10^5$ CFU/g of *M. furfur* fungi. As set forth in the table below, 24 hours after Formulation 1 was topically administered, the amount of *M. furfur* fungi remaining was $5.3 \times 10^3$ CFU/g, for a log reduction of 2.1. This data shows that the topically administered roflumilast formulation (Formulation 1) was successful in reducing the amount of *M. furfur* fungi.

| Formulation 1: ARQ 154 Foam, 0.3% roflumilast (0.2% MP, 0.05% PP), Lot No: PGW-C 01127 | | | |
|---|---|---|---|
| | CFU/g | | |
| | Viability Control | 24 Hours | Log Reduction |
| *M. furfur* | $6.5 \times 10^5$ | $5.3 \times 10^3$ | 2.1 |

Example 2

A comparative formulation was made using a sample of ARQ 154 Foam, comprising only a vehicle (0.2% MP, 0.05% PP) (no roflumilast), hereinafter referred to as Comparative Formulation 1. Comparative Formulation 1 was topically administered to $6.5 \times 10^5$ CFU/g of *M. furfur* fungi. As set forth in the table below, 24 hours after Comparative Formulation 1 was topically administered, the amount of *M. furfur* fungi remaining was 5.6×10⁴ CFU/g, for a log reduction of 1.1. This data shows that the topically administered Comparative Formulation 1 was not as successful in reducing the amount of *M. furfur* fungi as the roflumilast formulation (Formulation 1).

| Comparative Formulation 1: ARQ 154 Foam, Vehicle (0.2% MP, 0.05% PP), Lot No: PGT-C 01231 | | | |
|---|---|---|---|
| | CFU/g | | |
| | Viability Control | 24 Hours | Log Reduction |
| *M. furfur* | $6.5 \times 10^5$ | $5.6 \times 10^4$ | 1.1 |

Example 3

A comparative formulation was made using a sample of ARQ 154 Foam, comprising only a vehicle (no preservatives and no roflumilast), hereinafter referred to as Comparative Formulation 2. Comparative Formulation 2 was topically administered to $6.5 \times 10^5$ CFU/g of *M. furfur* fungi. As set forth in the table below, 24 hours after Comparative Formulation 2 was topically administered, the amount of *M. furfur* fungi remaining was $3.2 \times 10^4$ CFU/g, for a log reduction of 1.3. This data shows that the topically administered Comparative Formulation 2 was not as successful in reducing the amount of *M. furfur* fungi as the roflumilast formulation (Formulation 1).

| Comparative Formulation 2: ARQ 154 Foam, Vehicle (No Preservatives), Batch Lot No: 2020-091-02 | | | |
|---|---|---|---|
| | CFU/g | | |
| | Viability Control | 24 Hours | Log Reduction |
| *M. furfur* | $6.5 \times 10^5$ | $3.2 \times 10^4$ | 1.3 |

EXAMPLES 1-3 thus illustrate that topically administered roflumilast is a quick and effective antifungal agent, and presents a viable alternative to conventional topical antifungal formulations.

Example 4

Roflumilast creams were prepared according to the following formulations.

| Formulation A | |
|---|---|
| Roflumilast | 0.3% w/w |
| White Petrolatum | 10.0% w/w |
| Isopropyl Palmitate | 5.0% w/w |
| Crodafos CES (blend of cetearyl alcohol, dicetyl phosphate, ceteth-10 phosphate) | 10.0% w/w |
| Diethylene glycol monoethyl ether (Transcutol P) | 25% w/w |
| Methylparaben | 0.2% w/w |
| Propylparaben | 0.05% w/w |
| Purified Water | q.s. ad 100 (49.45%) |

| Formulation B | |
|---|---|
| Roflumilast | 0.3% w/w |
| White Petrolatum | 10.0% w/w |
| Isopropyl Palmitate | 5.0% w/w |
| Crodafos CES (blend of cetearyl alcohol, dicetyl phosphate, ceteth-10 phosphate) | 10.0% w/w |
| Hexylene glycol | 2.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (47.45%) |

Example 5

In Vitro Susceptibility of *Malassezia* Species to Roflumilast

The in vitro susceptibility of *Malassezia* species to roflumilast was determined utilizing three *Candida* species as internal control isolates for all testing. These three isolates were *C. albicans* American Type Culture Collection (ATCC) 90028, *C. krusei* (ATCC 6258) and *C. parapsilosis* (ATCC 22019). In addition to testing roflumilast all susceptibility assays were conducted using ketoconazole and hydrocortisone as positive and negative control compounds, respectively. All assays were placed within a humidified incubator set to 32° C. for a total of seven days. Each assay was evaluated after 12 hours of incubation and, every 24 hours post incubation for a total of seven days. The assays were evaluated for visual growth of each pathogen in the no treatment control as well as determination of minimum inhibition concentration (MIC) values. The concentration that provides a 3-$\log_{10}$ CFU/mL reduction in fungal burden from baseline at day 0 was defined as the minimum fungicidal concentration (MHC) and was determined by quantifying fungal burdens found in the microplate at day seven.

The method of Rojas (Rojas F D, et al. Antifungal susceptibility of *Malassezia furfur*, *Malassezia sympodialis*, and *Malassezia globose* to azole drugs and amphotericin B evaluated using a broth microdilution method. 2014. Medical Mycology. 52:641-646) was used in which the liquid broth medium was RPMI 1640 with added 1.8% glucose, 1% peptone, 0.5% ox-bile, 0.5% malt extract, 1% glycerol, 0.5% Tween 40 and 0.05% Tween 80. Round bottom 96 well microplates were used. The inoculums were prepared in sterile saline and diluted to a final targeted concentration of $0.5 \times 10^5$ to $2.5 \times 10^5$ CFU/mL in supplemented RPMI. Data for the ketoconazole positive control and hydrocortisone negative control are shown in Table A. To verify that the modified liquid broth medium did not significantly alter ketoconazole susceptibility of the internal control isolates, the expected values published by the Clinical Laboratory Standards Institute (CLSI) can be compared to the values in Table A. The CLSI expected values were 0.12-1 (at 24 hours) and 0.25-1 (at 48 hours) for the internal control isolates *C. krusei* (ATCC 6258). As seen in Table A, ketoconazole was slightly less effective against *C. krusei* (ATCC 6258) isolates than expected based on the CLSI guidelines. For the internal control isolate *C. parapsilosis* (ATCC 22019) the expected CLSI values for ketoconazole of 0.03-0.25 (at 24 hours) and 0.06-0.5 (at 48 hours) did agree with the 2-day value (Table A) of 0.5. The negative control hydrocortisone showed no anti-fungal activity.

In Vitro Micro-Dilution Susceptibility Assay

TABLE A

Results from the in vitro micro-dilution susceptibility assay using the methodology of Rojas for testing the ketoconazole positive control and the hydrocortisone negative control.

| Isolate | Time (days) | | | | | | | |
|---|---|---|---|---|---|---|---|---|
| | 0.5 | 1 | 2 | 3 | 4 | 5 | 6 | 7 |
| Ketoconazole Positive Control (mg/L) | | | | | | | | |
| C. albicans (ATCC 90028) | NGO | 0.06 | 0.06 | 0.125 | 0.25 | 0.25 | 0.25 | 0.25 |
| C. krusei (ATCC 6258) | NGO | 4 | 8 | 16 | 16 | 16 | 32 | 32 |
| C. parapsilosis (22019) | NGO | 0.5 | 0.5 | 0.5 | 0.5 | 1 | 1 | 2 |
| M. furfur (ATCC 14521) | NGO | NGO | 0.03 | 0.06 | 0.06 | 0.06 | 0.06 | 0.25 |
| M. furfur (ATCC 12078) | NGO | NGO | 0.06 | 0.06 | 0.06 | 0.06 | 0.06 | 0.25 |
| M. furfur (ATCC 44344) | NGO | NGO | 0.125 | 0.125 | 0.125 | 0.25 | 0.25 | 0.125 |
| M. globose (ATCC MYA-4889) | NGO | NGO | NGO | NGO | NGO | NGO | NGO | NGO |
| M. restricta (ATCC MYA-4611) | NGO | NGO | NGO | NGO | NGO | NGO | NGO | NGO |
| Hydrocortisone Negative Control (mg/L) | | | | | | | | |
| C. albicans (ATCC 90028) | >1024 | >1024 | >1024 | >1024 | >1024 | >1024 | >1024 | >1024 |
| C. krusei (ATCC 6258) | >1024 | >1024 | >1024 | >1024 | >1024 | >1024 | >1024 | >1024 |
| C. parapsilosis (22019) | >1024 | >1024 | >1024 | >1024 | >1024 | >1024 | >1024 | >1024 |
| M. furfur (ATCC 14521) | NGO | NGO | >1024 | >1024 | >1024 | >1024 | >1024 | >1024 |
| M. furfur (ATCC 12078) | NGO | NGO | >1024 | >1024 | >1024 | >1024 | >1024 | >1024 |
| M. furfur (ATCC 44344) | NGO | NGO | >1024 | >1024 | >1024 | >1024 | >1024 | >1024 |
| M. globose (ATCC MYA-4889) | NGO | NGO | NGO | NGO | NGO | >1024 | >1024 | >1024 |
| M. restricta (ATCC MYA-4611) | NGO | NGO | NGO | NGO | NGO | >1024 | >1024 | >1024 |

NGO = No Growth Observed

As shown in Table B roflumilast provides antifungal activity against *Malassezia* species when compared to the hydrocortisone negative control. Roflumilast MIC values ranged between 32 and 128 mg/L on day 2. Roflumilast did not demonstrate antifungal activity against the tested *Candida* species using the method of Rojas.

TABLE B

Results from the in vitro micro-dilution susceptibility assay using the methodology of Rojas for testing roflumilast.
Roflumilast (mg/L)

| Isolate | Time (days) | | | | | | | |
|---|---|---|---|---|---|---|---|---|
| | 0.5 | 1 | 2 | 3 | 4 | 5 | 6 | 7 |
| C. albicans (ATCC 90028) | >1024 | >1024 | >1024 | >1024 | >1024 | >1024 | >1024 | >1024 |
| C. krusei (ATCC 6258) | 128 | 1024 | >1024 | >1024 | >1024 | >1024 | >1024 | >1024 |
| C. parapsilosis (22019) | 1024 | 1024 | >1024 | >1024 | >1024 | >1024 | >1024 | >1024 |
| M. furfur (ATCC 14521) | NGO | NGO | 64, 32, 128 | 64, 32, 128 | 64, 32, 128 | 64, 32, 128 | 64, 32, 128 | 64, 32, 128 |
| M. furfur (ATCC 12078) | NGO | NGO | 128 | 128 | 128 | 128 | 128 | 128 |
| M. furfur (ATCC 44344) | NGO | NGO | 64 | 64 | 64 | 64 | 64 | 64 |
| M. globose (ATCC MYA-4889) | NGO | NGO | 32 | 32 | 128 | 128 | 128 | 128 |
| M. restricta (ATCC MYA-4611) | NGO | NGO | 32 | 32 | 32 | 32 | 32 | 64 |

NGO = No Growth Observed

Example 6

Determining Levels of *Malassezia*

Seborrheic dermatitis is a common, chronic inflammatory skin disease characterized by erythematous, scaly plaques, often with a yellowish, oily, moist, and/or greasy appearance, affecting areas of sebaceous gland abundance. Frequently involved sites include the scalp (including retroauricular areas), eyebrows, ears, nasolabial folds, eyelids, trunk, and intertriginous areas.

Topical roflumilast was administered in the form of a 0.3% foam formulation to 10 subjects suffering from seborrheic dermatitis once daily for two weeks. Samples were obtained from two collection sites from each of the participants using four skin swabs. Two skin swabs were taken from treated areas and two were taken from untreated areas at two time points. The first time point was day 1 of the treatment to establish the baseline and the second time point was 15 days later. Samples were collected by swabbing (Zymo R1109 DNA/RNA Collection Tube w/Swab) a 2 cm×2 cm or 3 cm×3 cm surface area of the skin for 2-4 minutes with 2 swabs per collection sites (holding 2 swabs together) while also rotating the swabs. For untreated sites, samples were collected from the shoulder/posterior deltoid area. For treated areas, samples were collected from alar creases area on the face if there was seborrheic dermatitis (SD). If there was no SD present in this area, then the sample was collected from an area in the body that was most representative of the SD disease process. Samples were stored on site at −80° C. until shipment to Microbac Laboratories and shipped with dry ice. Samples were stored at Microbac Laboratories at −80° C. until processing.

Primer/probes for *Malassezia furfur, Malassezia globosa, Malassezia restricta* and *Malassezia* spp. appropriate for qPCR were identified in the peer-reviewed article "Real-Time PCR Identification of Six *Malassezia* Species" published in Current Microbiology volume 74 pages 671-677 in 2017. Controls were established through the procurement of *Malassezia furfur, Malassezia globosa, Malassezia restricta* cells from the American Type Culture Collection (ATCC) and synthetic DNA from Integrated DNA Technologies (IDT).

Preliminary testing and validation was accomplished by:

a. The generation of response curves by using known concentrations of each target.

b. The response curves were also used to determine the Limit of Detection (LOD) and Limit of Quantitation (LOQ) for the assays.

qPCR analysis was run using Microbac in house standard operating procedures. DNA extraction was accomplished using the Qiagen DNEasy kit (with modifications) and then the qPCR was run as a single analysis for each target on extracted DNA from each of the swabs from the subjects. During the initial analyses both gene copy (gc) number and Cycle threshold (Ct) values were analyzed. The results showed an order of magnitude decrease between treated baseline and treated day 15 samples while the untreated baseline and day 15 samples were roughly equivalent. Statistical significance was found for the treated sites. When using the qPCR probes appropriate for *Malassezia furfur, Malassezia globosa, Malassezia restricta* and overall *Malassezia* spp seven of the ten subjects experienced an order of magnitude decrease in *Malassezia* gene counts (*Malassezia furfur, Malassezia globosa* and/or *Malassezia restricta*) in the treated area over time. Nine subjects showed no changes in *Malassezia* gene counts in the untreated areas while one participant subject showed a decrease.

The invention claimed is:

1. A method of treating a fungal infection in a subject in need thereof, comprising administering to the subject a composition comprising an antifungal effective amount of roflumilast or a pharmaceutically acceptable salt thereof, wherein the fungal infection is caused by *Malassezia* spp.

2. The method according to claim 1, wherein said roflumilast is administered topically.

3. The method according to claim 1, wherein said *Malassezia* spp. is selected from the group consisting of *M. furfur*, *M. restricta*, and *M. globosa*.

4. The method according to claim 3, wherein said *Malassezia* spp. is *M. furfur*.

5. The method according to claim 1, wherein the fungal infection comprises fungal overgrowth of hair, skin or nails.

6. The method according to claim 1, wherein said subject is suffering from seborrheic dermatitis, dandruff, dupilumab facial redness, *Tinea versicolor, Pityriasis versicolor, Tinea circinata, Tinea pedis, Tinea unguium, Tinea manus, Tinea cruris, Tinea corporis, Tinea faciei, Tinea capitis*, or *Tinea incognito*.

7. The method according to claim 6, wherein said subject is suffering from seborrheic dermatitis.

8. The method according to claim 1, wherein said composition comprises carriers suitable for topical administration.

9. The method according to claim 1, wherein said composition is selected from the group consisting of an aerosol, a foam, a spray, an emulsion, a gel, a liquid, an ointment, a paste, a shampoo, a suspension, and a system.

10. The method according to claim 9, wherein said composition is a foam.

11. The method according to claim 1, wherein said composition comprises 0.3% w/w roflumilast.

12. The method according to claim 1, wherein said composition comprises roflumilast, white petrolatum, isopropyl palmitate, cetearyl alcohol, dicetyl phosphate, ceteth-10 phosphate, hexylene glycol, diethylene glycol monoethyl ether, methylparaben, propylparaben and water.

13. The method according to claim 1, wherein said composition consists of:

| | |
|---|---|
| roflumilast | 0.3% w/w |
| white petrolatum | 10.0% w/w |
| isopropyl palmitate | 5.0% w/w |
| cetearyl alcohol, dicetyl phosphate and ceteth-10 phosphate blend | 10.0% w/w |
| hexylene glycol | 2.0% w/w |
| diethylene glycol monoethyl ether | 25.0% w/w |
| methylparaben | 0.2% w/w |
| propylparaben | 0.05% w/w, and |
| purified water | q.s. ad 100 (47.45%). |

14. The method according to claim 1, further comprising administering an additional anti-fungal agent and/or an anti-inflammatory agent.

15. The method according to claim 14 wherein said additional anti-fungal agent is selected from the group consisting of: drugs containing miconazole, ciclopirox olamine, clotrimazole, butenafine, terbinafine, amorolfine, naftifine, tolnaftate, ketoconazole, efinaconazole, griseofulvin, imidazoles, triazole, voriconazole, benzimidazole, ethylparaben, flucytosine, salicylic acid, selenium sulfide, and undecylenic acid.

16. The method according to claim 14 wherein said additional anti-inflammatory agent is a corticosteroid or a calcineurin inhibitor.

17. A method of treating a fungal infection, fungal overgrowth and/or hypersensitivity to *Malassezia* spp in a subject in need thereof, comprising topically administering to the subject an antifungal effective amount of roflumilast or a pharmaceutically acceptable salt thereof, wherein the fungal infection or overgrowth is caused by *Malassezia* spp.

* * * * *